United States Patent
D'Onofrio et al.

(10) Patent No.: US 10,668,177 B1
(45) Date of Patent: Jun. 2, 2020

(54) SYSTEMS AND METHODS FOR AUTOCLAVE OPERATING EVALUATION AND VERIFICATION

(71) Applicant: Maxim Integrated Products, Inc., San Jose, CA (US)

(72) Inventors: Michael James D'Onofrio, Dallas, TX (US); Nicholas Bodnar, Durham, NC (US)

(73) Assignee: Maxim Integrated Products, Inc., San Jose, CA (US)

(*) Notice: Subject to any disclaimer, the term of this patent is extended or adjusted under 35 U.S.C. 154(b) by 239 days.

(21) Appl. No.: 15/840,796

(22) Filed: Dec. 13, 2017

Related U.S. Application Data

(60) Provisional application No. 62/433,473, filed on Dec. 13, 2016.

(51) Int. Cl.
| | |
|---|---|
| *G21C 17/112* | (2006.01) |
| *G06F 11/30* | (2006.01) |
| *A61L 2/24* | (2006.01) |
| *A61L 2/07* | (2006.01) |
| *G01M 99/00* | (2011.01) |
| *B08B 5/00* | (2006.01) |
| *B08B 3/00* | (2006.01) |

(52) U.S. Cl.
CPC .............. *A61L 2/07* (2013.01); *G01M 99/008* (2013.01); *A61L 2202/14* (2013.01); *B08B 3/00* (2013.01); *B08B 5/00* (2013.01); *B08B 2230/01* (2013.01)

(58) Field of Classification Search
CPC .... A61L 2/07; A61L 2202/14; G01M 99/008; B08B 3/00; B08B 5/00; B08B 2230/01
USPC .......... 702/81, 84, 98, 99, 182; 422/3, 6, 28, 422/112, 116
See application file for complete search history.

(56) References Cited

U.S. PATENT DOCUMENTS

| | | | |
|---|---|---|---|
| 7,935,306 B2 | 5/2011 | Klun | |
| 8,641,965 B2 | 2/2014 | Martel et al. | |
| 2003/0133830 A1* | 7/2003 | Gonzalez | A61L 2/28 422/28 |
| 2007/0202004 A1* | 8/2007 | Martel | A61L 2/07 422/3 |
| 2008/0138253 A1* | 6/2008 | Golder | A61L 2/07 422/112 |
| 2015/0374868 A1 | 12/2015 | Bruce et al. | |
| 2016/0004956 A1* | 1/2016 | Reynolds | G06M 1/02 377/15 |

* cited by examiner

*Primary Examiner* — John H Le
(74) *Attorney, Agent, or Firm* — Michael North; North Weber & Baugh LLP

(57) ABSTRACT

Systems and methods are described for logging parameter data in autoclave operating cycles. The system has capacity to compensate the response delay to thereby accurately track the ambient gas parameters, such as temperature, pressure, humidity, sterilization gas density, within the autoclave during operation. By properly correcting for the thermal delay, the data accuracy of the measured gas temperature is thus greatly enhanced. Methods for evaluating and verifying autoclave operation cycle are also described. Furthermore, the system may also be used for autoclave pre-maintenance and performance trend analysis.

20 Claims, 11 Drawing Sheets

SYSTEMS AND METHODS FOR AUTOCLAVE OPERATING EVALUATION AND VERIFICATION

CROSS REFERENCE TO RELATED PATENT APPLICATIONS

The present application claims priority benefit, under 35 U.S.C. § 119(e), to commonly assigned U.S. Provisional Patent Application No. 62/433,473, entitled "Systems and Methods for Autoclave Operating Evaluation and Verification," naming as inventors Michael James D'Onofrio and Nicholas Bodnar, and filed Dec. 13, 2016, which application is hereby incorporated herein by reference in its entirety and for all purposes.

BACKGROUND

A. Technical Field

The present invention relates to autoclave monitoring, and more particularly, to systems and methods for logging parameter data in autoclave operating cycles.

B. Background of the Invention

An autoclave is a chamber used to implement industrial processes, typically at elevated temperature and/or pressure than ambient air temperature/pressure. Autoclaves are used in various applications, such as medical filed or chemical industry, to perform sterilization or cure coatings and/or promote hydrothermal synthesis, etc.

There are physical, chemical, and biological indicators that can be used to ensure that an autoclave reaches the correct temperature for the correct amount of time. If an item is not treated properly, it may cause serious risk, such as in the application of surgery tool sterilization.

Some physical indicators use an alloy designed to melt only after being subjected to a given temperature for the relevant holding time. If the alloy melts, the change will be visible. Chemical indicators, typically used on medical packaging or autoclave tape, change color once the correct conditions being met to indicate appropriate processing for the object inside the package or under the tape. Biological indicators may be used to prove sterility. Biological indicators contain spores of a heat-resistant bacterium, such as Geobacillus stearothermophilus. If the autoclave does not reach the right temperature, the spores will germinate when incubated and their metabolism will change the color of a pH-sensitive chemical.

Some steam sterilization cycles may comprise one or more intervals with desired temperature and time for each interval. For example, in the Guideline for Disinfection and Sterilization in Healthcare Facilities 200, the Centers for Disease Control and Prevention (CDC) provides Minimum cycle times for steam sterilization cycles (in Table 7, page 112). The steam sterilization cycles for Wrapped instruments under Gravity displacement comprises an interval of 30 minutes of exposure time at 121° C. (250° F.), an interval of 15 minutes of exposure time at 132° C. (270° F.) and a dry time between 15 and 30 minutes (Table 7, page 112, www.cdc.gov/hicpac/pdf/guidelines/Disinfection_Nov_2008.pdf).

Biological indicators may provide an end result without identifying the accuracy of each specific interval for the entire sterilization process.

Furthermore, some conventional devices for logging temperature data have been designed to operate at relatively large time interval. For instance, a typical device for monitoring the ocean temperature may have a water-proof capsule and take a sample at every hour. Typically, the capsule is made of thick metal plate, and there is a time lag between the ocean water and the temperature inside the capsule. In such a case, the time constant for the device is in the order of minute, and thus, the time lag due to the large thermal mass of the capsule may not affect the accuracy of the data.

In applications such as autoclave for steam sterilization, the time interval is relatively short since the ambient gas temperature inside the autoclave rises from room temperature to 100° C. quite quickly. When a conventional device for logging temperature data is placed inside the autoclave, the device may not be able to keep up with the temperature change due to the thermal resistance of the data logger package. The thermal resistance may result in false reading of the ambient gas temperature. For instance, the conventional device may take longer to heat up relative to the ambient gas in the autoclave than to cool down relative to the ambient gas. As a result, the device may indicate that the autoclave is maintained at the intended sterilization temperature shorter than it actually does. As such, there is a need for a device for electronically logging temperature data (as well as other applicable ambient gas parameters, such as pressure, humidity, etc.), where the time constant of the data logger package is short enough to accurately keep track of the ambient gas parameters.

As such, there is also a need for systems and methods for logging parameter data in autoclave operating cycles and with the capacity to correct the delay to thereby accurately track the ambient gas parameters.

BRIEF DESCRIPTION OF THE DRAWINGS

References will be made to embodiments of the invention, examples of which may be illustrated in the accompanying figures. These figures are intended to be illustrative, not limiting. Although the invention is generally described in the context of these embodiments, it should be understood that it is not intended to limit the scope of the invention to these particular embodiments.

DETAILED DESCRIPTION OF THE PREFERRED EMBODIMENTS

In the following description, for the purposes of explanation, specific details are set forth in order to provide an understanding of the invention. It will be apparent, however, to one skilled in the art that the invention can be practiced without these details. One skilled in the art will recognize that embodiments of the present invention, described below, may be performed in a variety of ways and using a variety of means. Those skilled in the art will also recognize additional modifications, applications, and embodiments are within the scope thereof, as are additional fields in which the invention may provide utility. Accordingly, the embodiments described below are illustrative of specific embodiments of the invention and are meant to avoid obscuring the invention.

A reference in the specification to "one embodiment" or "an embodiment" means that a particular feature, structure, characteristic, or function described in connection with the embodiment is included in at least one embodiment of the invention. The appearance of the phrase "in one embodiment," "in an embodiment," or the like in various places in the specification are not necessarily all referring to the same embodiment.

Connections illustrated in the figures between components may be modified or otherwise changed through the addition thereto of intermediary components, without departing from the teachings of the present invention.

Furthermore, one skilled in the art shall recognize: (1) that certain steps may optionally be performed; (2) that steps may not be limited to the specific order set forth herein; and (3) that certain steps may be performed in different orders, including being done contemporaneously.

Figure 1A:
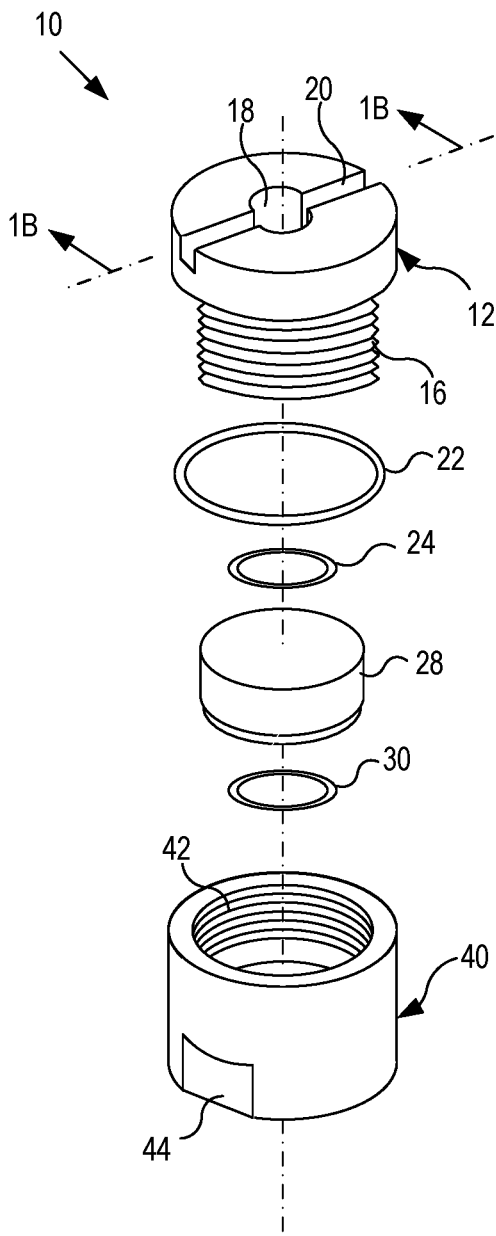
FIGS. 1A-1C show a package for logging temperature data according to embodiments of the present invention.
Figure 1B:
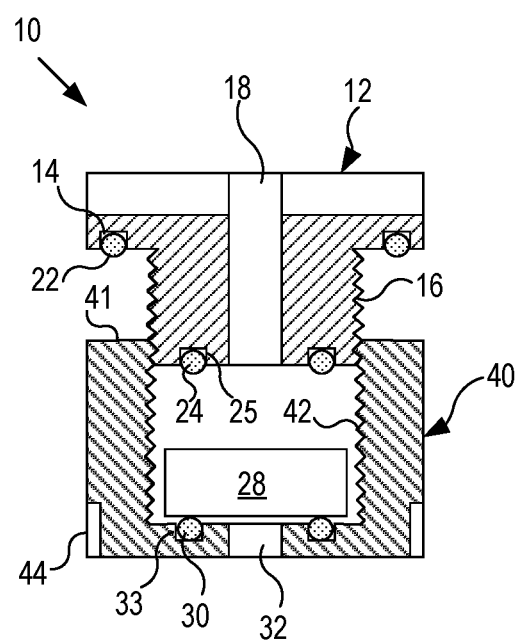
Figure 1C:
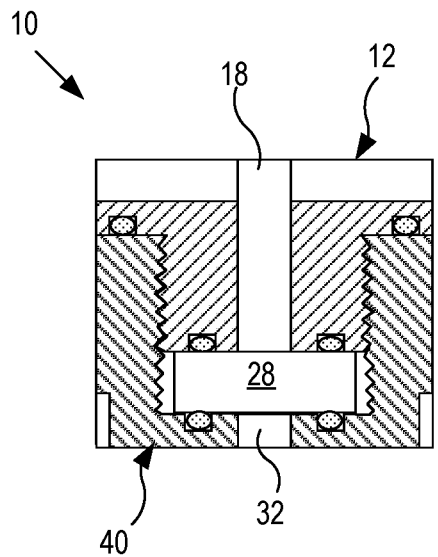

FIG. 1A shows an exploded view of a package 10 for logging temperature data according to embodiments of the present invention. As depicted in FIG. 1A, the package 10 includes: a capsule having a plug 12, a base 40 and O-rings 22, 24, and 30; and a temperature data logger (or, shortly, data logger) 28 for logging temperature data under harsh environments. In embodiments, the data logger 28 may be an integrated circuit (IC)-based temperature data logger. FIG. 1B shows a cross sectional view of the package 10, taken along the direction 1B-1B, where the male thread 16 of the plug 12 is slightly engaged into the female thread 42 of the base 40. FIG. 1C shows the package 10, where the plug 12 is fully engaged into the base 40.

For the purpose of illustration, the package 10 is described as a temperature data logging device that may also log pressure or humidity for a steam autoclave chamber, i.e., the package 10 is mounted inside a steam autoclave chamber and logs temperature data during sterilization cycles of the autoclave. For instance, an exemplary operational condition of the steam autoclave has the temperature of 140° C. and the pressure of 2 atmosphere, and each cycle may last 35-40 minutes, and the package 10 is designed to survive more than hundred cycles without being damaged by the ambient gas. However, it should be apparent to those of ordinary skill in the art that the package 10 may be applied to other test environments. Also, it should be apparent to those of ordinary skill in the art that the package 10 may be calibrated to accommodate different operational temperature ranges.

The plug 12 includes: a slot 20 for receiving a tool, such as torque wrench, for turning the plug 12 relative to the base 40; and a through hole 18 that allows the ambient gas to directly contact the top surface of the data logger 28 during operation. Since the ambient gas including hot steam is in direct contact with the data logger 28, the thermal lag between the chamber environment and the data logger 28 is reduced so that the data logger 28 can accurately track the temperature variation inside the chamber.

The O-rings 22, 24, and 30 are used to prevent ingress of moisture into the data logger 28. The O-ring 22 rests on a groove 14 that is formed on the plug 12. The O-ring 22 is compressed by the lip 41 of the base 40 when the plug 12 is fully engaged into the base 40, as shown in FIG. 1C, to thereby preventing ingress of the ambient gas through the gap between the male thread 16 and the female thread 42.

The O-rings 24 and 30 rest on grooves 25 and 33, respectively. When the package 10 is assembled, the O-rings 24 and 30 are compressed by the top and bottom surfaces of the data logger 28, respectively, to thereby prevent ingress of the ambient gas through the gaps between the capsule and the data logger 28.

The base 40 includes a through hole 32 that allows the ambient gas to directly contact the bottom surface of the data logger 28 during operation. Since the ambient gas is in direct contact with the data logger 28, the thermal lag between the chamber environment and the data logger 28 is reduced so that the data logger 28 can accurately track the temperature variation inside the chamber. The base 40 also includes a notch/recess 45 so that a proper device securely holds the base in place during assembly of the package 10.

If the package 10 is assembled while the O-rings 22, 24, and 30 are dry, the O-rings may not properly seal the space surrounding the data logger 28 due to pinching, crimping, or twisting of the O-rings. To avoid such deformation of the O-rings, small amount of grease is applied to the O-rings. The grease also holds the O-rings in their corresponding grooves temporarily during assembly. For instance, the O-rings 22 and 24 remain seated on the grooves 14 and 25, respectively, by the grease when the plug 12 is flipped over during assembly, as shown in FIG. 1B.

It is noted that the package 10 may be mounted in the autoclave chamber with other items, such as medical instruments, being sterilized. If the package 10 releases any toxic material into the autoclave chamber, the items may be contaminated by the toxic material. As such, all of the components, including the grease, of the package 10 are tested to ensure that none of the components release toxins during sterilization cycles.

The capsule is reusable, i.e., the user can disengage the male thread 16 from the female thread 42, replace the data logger 28, and reassemble the package 10. During this process, the user may not place one or more of the O-rings 22, 24 and 30 properly i.e., the user may misalign the O-rings on resealing. In embodiments, to obviate the improper reassembly by the user, small amount of glue may be applied to the threads so that the plug and base are glued together.

Figure 2:
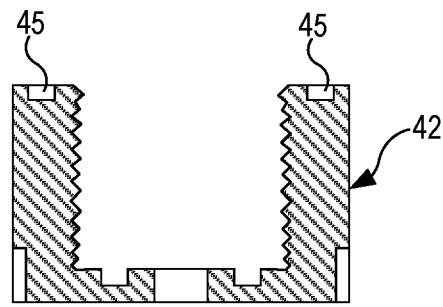
FIG. 2 shows a cross sectional view of a base of a capsule according to embodiments of the present invention.

FIG. 2 shows a cross sectional view of a base 42 of a capsule according to embodiments of the present invention. As depicted, the base 42 is similar to the base 40 in FIGS. 1A-1C, with the difference that the base 42 includes an O-ring groove 44 that the O-ring 22 rests on. It should be apparent to those of ordinary skill in the art that the package 10 may include other suitable types of sealing mechanisms to prevent the ingress of the ambient gas into the data logger 28.

The material for the plug 12 and base 40 (or 42) may be chosen for its mechanical properties (i.e., they remain stable during both long and short-term exposure to high temperature and pressure), inherent flame resistance, and outstanding chemical resistance (i.e., inert to high temperature steam, strong bases, fuels and acids). In embodiments, the plug and base are formed of a polymer, such as polyphenylene sulfide (PPS). Likewise, the material for the O-rings 22, 24, and 30 may be chosen for their mechanical strength and chemical qualities. In embodiments, the O-rings are formed of silicon, where the silicon O-rings are also resistant to sunlight, ozone, oxygen, and UV light.

Figure 3:
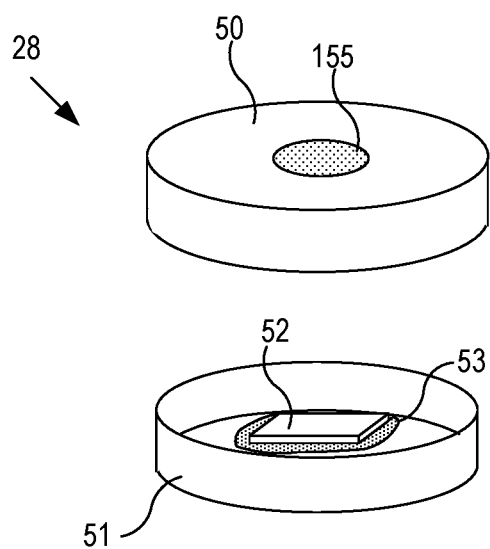
FIG. 3 shows an integrated circuit (IC)-based temperature data logger according to embodiments of the present invention.

FIG. 3 shows an integrated circuit (IC)-based temperature data logger 28 according to embodiments of the present invention. As depicted, the temperature logger 28 includes: a top cover 50; a bottom cover 51; an electrical circuitry 52 for measuring and storing the temperature data; and a securing element 53 that secures the electrical circuitry 52 to the bottom cover 51. When the data logger 28 is assembled, the top and bottom covers 50 and 51 form a housing and the electrical circuitry 52 is disposed in the inner space of the housing. In embodiments, the top and bottom covers 50 and 51 may provide water-proof sealing against fluid.

In embodiments, the top and bottom covers 50 and 51 may be formed of electrically conducting material and operate as two electrodes that are electrically connected to the electrical circuitry 52. For instance, a suitable electrical device may communicate the data logged in the data logger 28 through the top and bottom covers 50 and 51, or through a wireless communication interface integrated within the electrical circuitry 52. The top and bottom covers 50 and 51 are formed of material having high thermal conductivity, such as metal, so that the lag between the temperature of the autoclave chamber and the temperature inside the covers 50 and 51 is minimized. The securing element 53 is formed of material having a high thermal conductivity, such as heat conducting glue, to minimize the thermal lag between the temperature inside the covers 50 and 51 and the temperature outside the covers.

Unlike the conventional temperature loggers, a portion 155 of the top cover 50 is directly exposed to the ambient gas via the through hole 18 without damaging the electric circuitry 52 during operation. Likewise, a portion of the bottom cover 51 is directly exposed to the ambient gas via the through hole 32 during operation. This feature allows the data logger 28 to have minimal temperature lag, i.e., the data logger 28 can track the ambient gas temperature more accurately.

Figure 4:
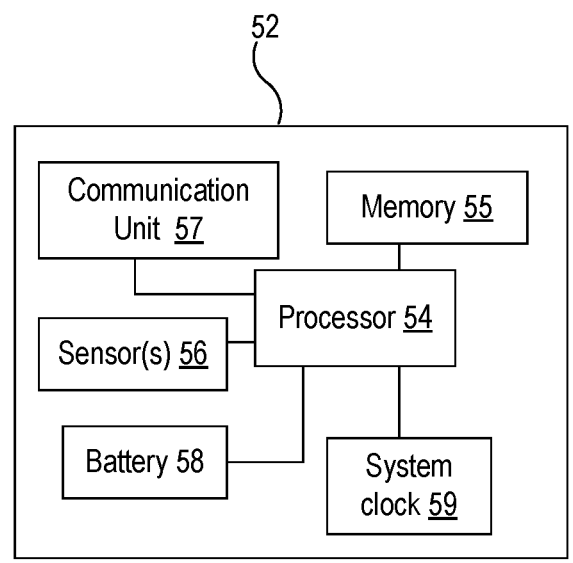
FIG. 4 shows a schematic diagram of an electric circuitry of the IC-based temperature data logger in FIG. 3 according to embodiments of the present invention.

FIG. 4 shows a schematic diagram of the electronic circuitry 52 of the IC-based temperature data logger 28 in FIG. 3 according to embodiments of the present invention. In embodiments, the electrical circuitry 52 may be an application-specific integrated circuit (ASIC) and include: a processor 54 for operating various components of the circuitry 52; sensor(s) 56 for measuring one or more ambient gas parameters (such as temperature, pressure, humidity, gas chemistry, etc.); a battery 58 for providing electrical power to the circuitry 52; a communication unit 57 for communicating data to an external device; a memory 55 for storing the measured temperature data; and a system clock 59 for generating clock signals for the circuitry 52. It is noted that, depending on the application, the circuitry 52 may include additional components, such as additional sensors, and one or more of the components of the circuitry 52 may be omitted. In embodiments, some special treatment gas may be added to enhance the sterilization effects. For example, hydrogen peroxide may be introduced into the autoclave to further sterilize the items within the autoclave. In embodiments, the sensor 56 may be a temperature, a pressure sensor, a humidity sensor, an oxygen sensor, a hydrogen peroxide ($H_2O_2$) sensor, an ethylene oxide (ETO) sensor, or a combination thereof.

In embodiments, the processor 54 may be programmed to measure the temperature (and/or pressure, humidity or other parameters) inside the data logger 28 at a preset time and/or repeat measurements at a preset time interval. In embodiments, the processor 54 may receive the clock signals from the system clock 59 and cause the sensor 56, such as digital temperature sensor, to measure the temperature as scheduled. Then, the processor 54 may store the data into the memory 55, where the memory 55 may be a static RAM, for instance. In embodiments, to minimize the power consumption, the processor 54 may wake up at the scheduled time to measure the temperature and goes back to sleep mode after measurement is completed.

Figure 5:
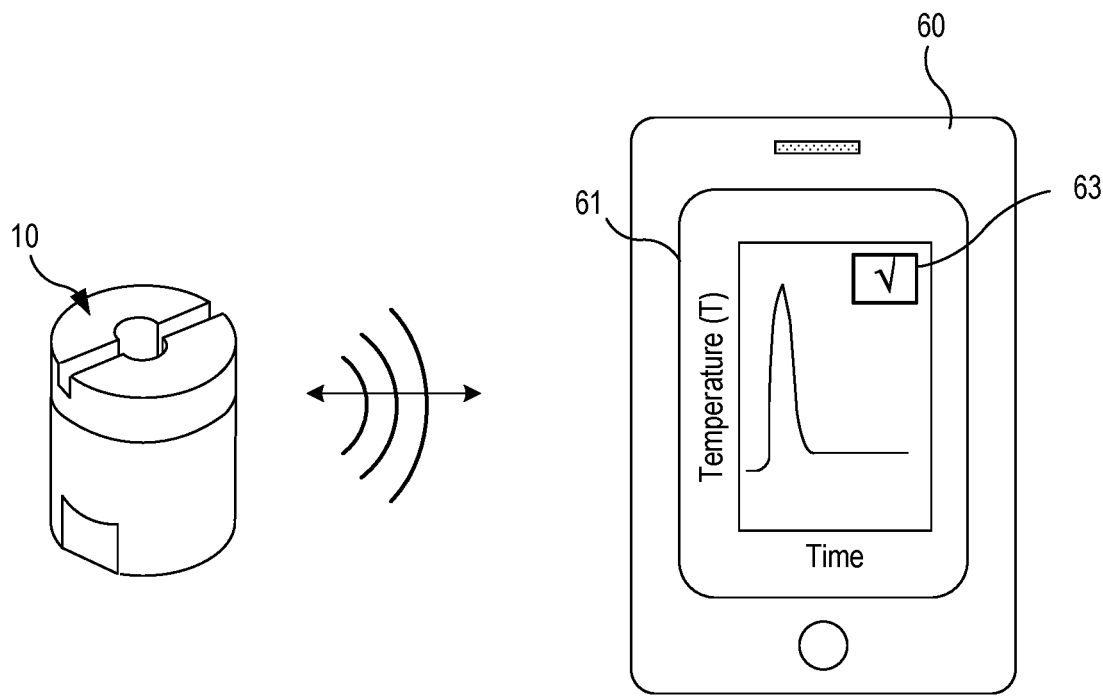
FIG. 5 shows a data communication between the package in FIG. 1A and a mobile device according to embodiments of the present invention.

In embodiments, the processor 54 may communicate the stored data to an external device through the communication device 57 and/or the processor 54 may be controlled/programmed through the communication device 57. In embodiments, the communication unit 57 may be a wireless communication device. FIG. 5 shows a data communication between the package 10 and a mobile device 60 according to embodiments of the present invention.

In embodiments, the user may install an application on the mobile device 60 so that the user can set up the parameters on the circuitry 52, such as time and frequency of data sampling, target temperature, pressure, and/or humidity before the package 10 is mounted in the autoclave. After a sterilization cycle(s), the user may retrieve the stored data from the package 10 using the mobile device 60 and a suitable application may display the temperature, pressure, and/or humidity data on the display 61 of the mobile device 60. In some embodiments, the display 61 also displays a pass/fail icon 63 corresponding to a passing or failed examination result for the retrieved data. It is noted that the user may control and communicate to the package 10 using other suitable external devices. For instance, in embodiments, the user may use a computer/server in place of the mobile device 60.

Figure 6:
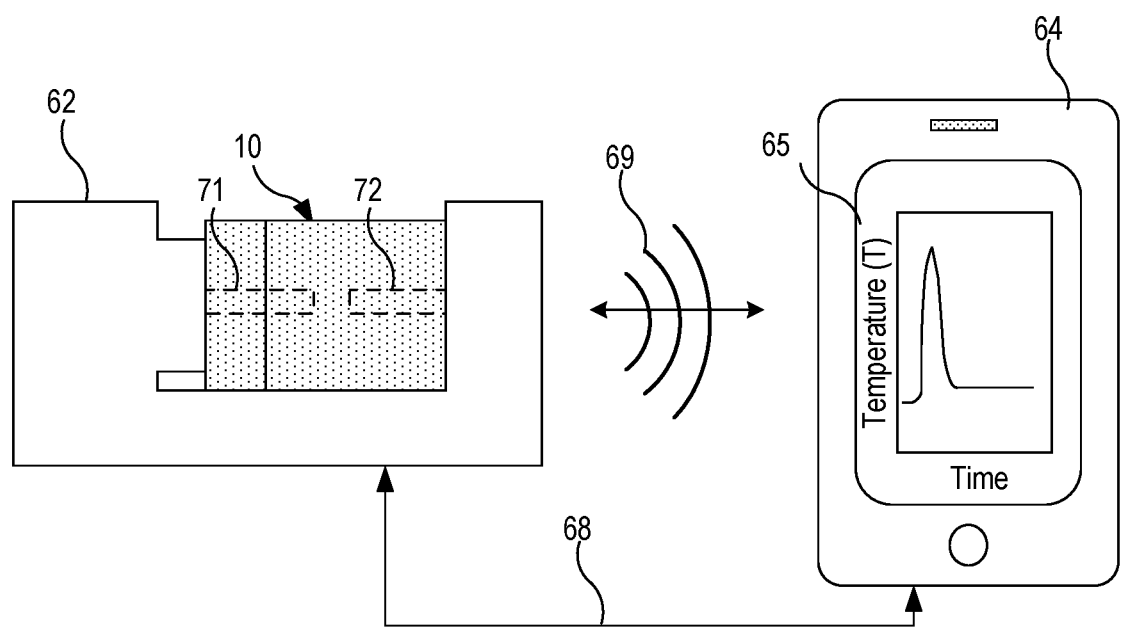
FIG. 6 shows a data communication between the package in FIG. 1A and a mobile device according to embodiments of the present invention.

FIG. 6 shows a data communication between the package 10 and a mobile device 64 according to embodiments of the present invention. As depicted, the package 10 may be docked in a reader 62 that can retrieve data stored in the package 10 and send the retrieved data to the mobile device 64. In embodiments, the reader 62 may have two springloaded electrodes 71 and 72 that make electrical contact to the top and bottom surfaces of the data logger 28, respectively, and extract the data stored in the package 10. Also, in embodiments, the reader 62 may be used to transmit electrical signals from the mobile device 64 to the package 10 so that the user can program the electrical circuitry 52.

After a sterilization cycle(s), the user may retrieve the stored data from the package 10 using the mobile device 64 and a suitable application installed in the mobile device 64 displays a pass or fail of the cycle based on the temperature data and/or pressure and humidity data on the display 65 of the mobile device 64. It is noted that the user may control and communicate to the package 10 using other suitable external device. For instance, in embodiments, the user may use a computer/server in place of the mobile device 64. In some embodiments, the reader 62 may exchange electrical signals with the mobile device 64 through wireless communication 69, as shown in FIG. 6, or through wire 68, such as universal serial bus (USB) connection. In some embodiments, the package itself may provide a pass or fail determination of the cycle based on temperature data and/or pressure and humidity data without assistance of another device via using its own internal decision algorithm. In some embodiments, to alert the user of the result, the package may use a green or red LED to indicate pass or fail, respectively. Alternatively, the package may still transfer the raw parametric data to an external device where an algorithm on the external device makes the pass or fail decision, but this decision is relayed back to the original package and the corresponding green or red LED is shown based upon the pass or fail decision.

Figure 7:
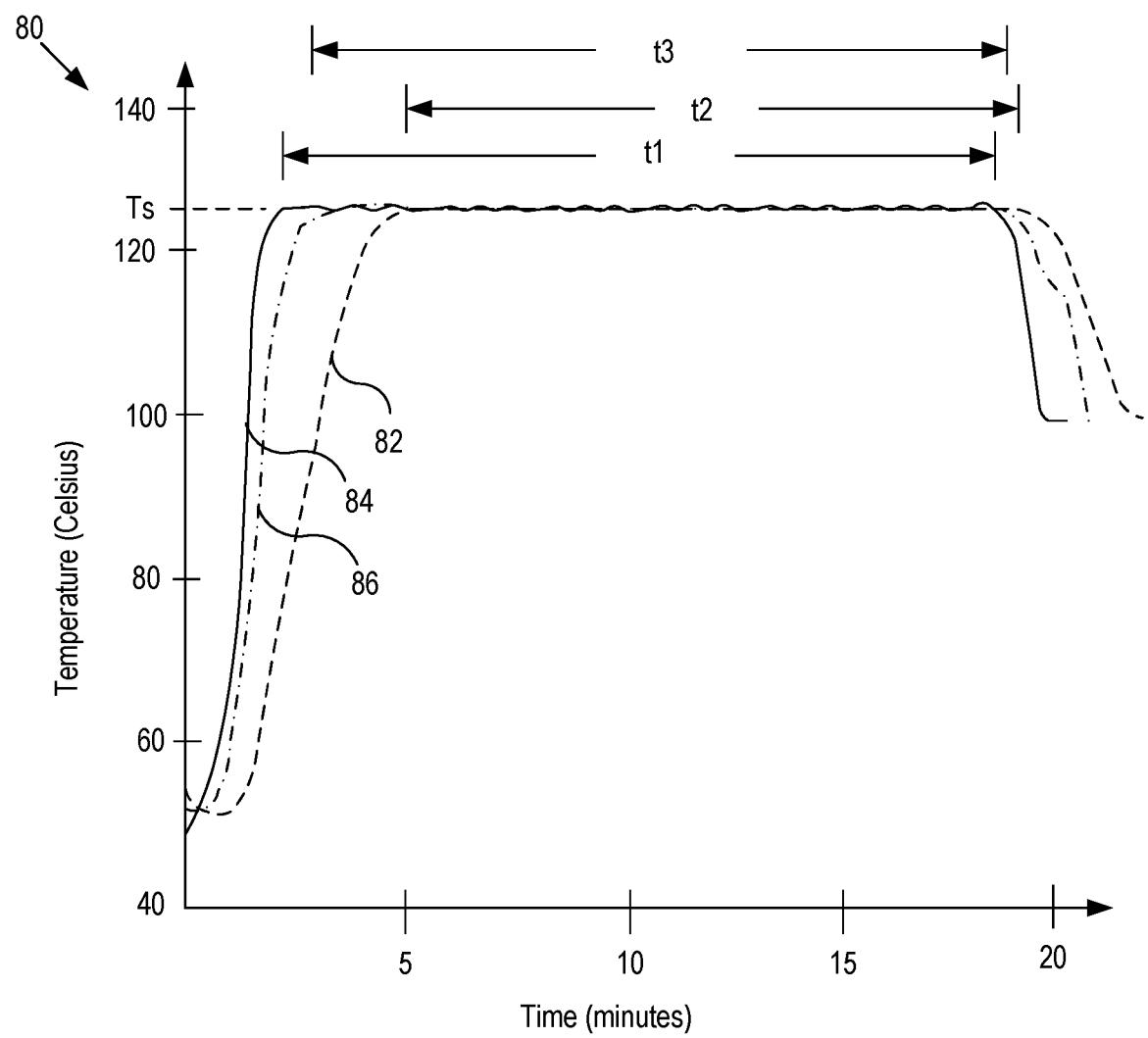
FIG. 7 shows a plot of temperature with and without correction according to embodiments of the present invention.

FIG. 7 shows an exemplary plot of ambient gas temperature 84 and the temperature 82 measured by the package 10 during a sterilization cycle according to embodiments of the present invention. As depicted, there is a lag between the ambient gas temperature 84 and the measured temperature 82, i.e., the measured temperature 82 shows that the ambient gas reaches the target sterilization temperature, Ts, several minutes after the ambient gas actually reached Ts. In FIG. 7, t1 represents the time interval during which the ambient gas is actually maintained at Ts while the measured temperature 82 indicates that the ambient gas is maintained at Ts during the time interval t2. For the purpose of illustration, it is assumed that t1 is longer than the required time interval for proper sterilization while t2 is shorter than the required time interval for proper sterilization. If the pass/fail test of the sterilization cycle is determined based on whether the ambient gas is maintained at Ts longer than the required time interval, the measured temperature 82 may indicate that the sterilization cycle failed the test, while the sterilization cycle actually passed the test.

To correct the lag, the mobile device 60, computer/server, or any other computing device may have a software program (or, shortly, algorithm) that analyzes the measured temperature 82. In embodiments, the algorithm may be based on phenomenological model of heat transfer between ambient gas (A) and probe/sensor (P) 56 via the probe enclosure (E), where the enclosure may collectively refer to the plug 12, base 40, and top and bottom covers 50 and 51.

Assuming that the enclosure temperature $T_E$ differs from both actual ambient gas temperature $T_A$ and probe temperature $T_P$, the rate of heat transfer between the probe enclosure and the probe is expressed as:

$$Cp\frac{dTp}{dt} = k_1(T_E - Tp) \tag{1}$$

where, the parameters $C_p$ and $k_1$ are the heat capacity and heat transfer coefficient of the probe, respectively.

Likewise, the rate of heat transfer between the ambient gas and probe enclosure is expressed as:

$$C_E\frac{dT_E}{dt} = k_2(T_A - T_E) \tag{2}$$

where, the parameters $C_E$ and $k_2$ are the heat capacity and heat transfer coefficient of the probe enclosure, respectively.

Combining Eq. (1) and Eq. (2), the relation between the ambient gas temperature $T_A$ and the probe temperature $T_P$ is expressed as:

$$T_A = Tp + (\tau_1 + \tau_2)\frac{dTp}{dt} + (\tau_1\tau_2)\frac{d^2Tp}{dt^2} \tag{3}$$

where, $\tau_1$ (=$C_p$/k1) and $\tau2$ (=$C_E$/k2) are time constants for the probe and probe enclosure, respectively. In embodiments, several factors may affect the actual values of the time constants, τ1 and τ2.

Although FIG. 7 shows ambient gas temperature 84 and the measured temperature 82, and the compensated temperature 86, it might be applicable for one with ordinary skill in the art may that the compensation method to obtain the compensated temperature may also be applied for measurement of other ambient gas parameters, such as gas pressure, humidity, gas chemistry such as oxygen or hydrogen peroxide density, etc. The vertical axis as shown in FIG. 7 may also be a pressure, humidity, oxygen density, hydrogen peroxide density, etc. One of ordinary skill in the art will also understand that the measured parameter may have a different profile. For example, the pressure may be lowered in the initial transition period and then be maintained at a desired low-pressure value for a predetermined time, and be received to normal pressure (such as atmospheric pressure).

Figure 8:
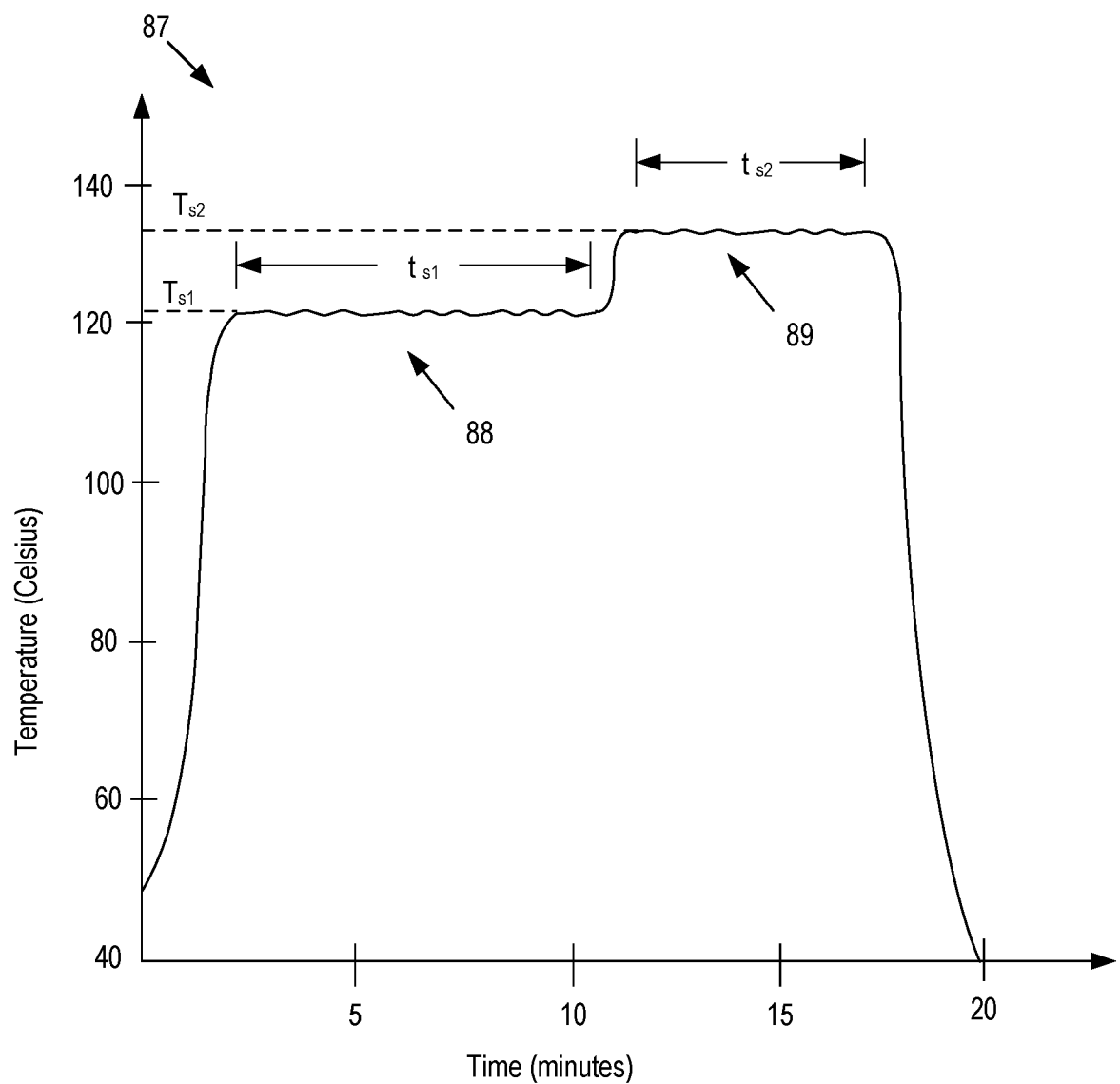
FIG. 8 shows a plot of temperature for an exemplary cycle with two intervals according to embodiments of the present invention.

In embodiments, a sterilization process may comprise one or more cycles with different temperature and time requirements for each cycle. In embodiments, a sterilization cycle may comprise one or more time periods (or intervals) with desired temperature and time for each period. FIG. 8 shows an exemplary cycle 87 with two intervals according to embodiments of the present invention. The cycle comprises a first interval 88 and a second interval 89. The first interval 88 has a required temperature Ts1 and a time interval is 1 during which the target sterilization temperature Ts1. The second interval 89 has a required temperature Ts2 and a time interval ts2 during which the target sterilization temperature Ts2. Although FIG. 8 depicts only two intervals with different temperature and time settings for each interval, one of ordinary skill in the art will understand that one cycle may comprise more than two intervals with different requirements for each interval. One of ordinary skill in the art will also understand that the following intervals may have lower temperature requirement than the initial interval, as contrary to FIG. 8. One of ordinary skill in the art will understand that the cycle with different temperature intervals as shown in FIG. 8 may also be applicable to process cycles with different intervals for other or different parameters, such as pressure, humidity, oxygen density, hydrogen peroxide density, etc. One of ordinary skill in the art will understand that the cycle comprising different intervals with each interval having specific combination of gas parameters, such as temperature and pressure, etc.

Physical, chemical or biological indicators may provide an end result without identifying the accuracy of each specific interval for the entire sterilization cycle.

Figure 9:
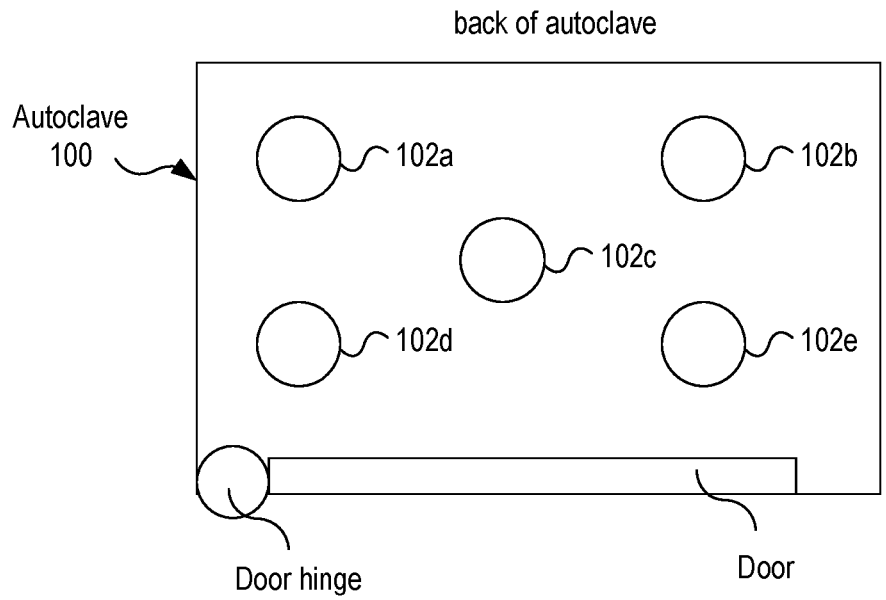
FIG. 9 shows packages inside an autoclave according to embodiments of the present invention.

FIG. 9 shows several devices under test (DUT) 102*a*-102*e* located inside an autoclave 100 according to embodiments of the present invention. In embodiments, each of the DUT 102 may be similar to the package 10. As depicted, depending on the locations where the DUT 102 are installed, the time constants ($\tau 1$ and $\tau 2$) of each device may have different values. In embodiments, the devices 102*a*-102*e* are used to measure the same parameter(s), such as temperature, pressure, humidity, ambient $O_2$ or $H_2O_2$ density, etc. In embodiments, the devices 102*a*-102*e* are used to measure different parameters. For example, device 102*a* may be used for temperature monitoring, device 102*b* may be used for pressure monitoring, device 102*c* may be used for ambient humidity monitoring, device 102*c* may be used for ambient $O_2$ density monitoring, and device 102*d* may be used for $H_2O_2$ density monitoring. All the information related to respective monitored parameter is then integrated together for an overall examination of the sterilization process.

The time constants corresponding to the devices 102*a*-102*e* may or may not be the same. In embodiments, the values of the time constants may vary depending on other parameters: (1) whether the package is bagged or unbagged in a pouch during the sterilization cycle; (2) whether the autoclave is unloaded or loaded with other items, such as medical instruments, during the sterilization cycle; (3) whether the autoclave was warm before the cycle; (4) the type of cycles, such as vacuum or gravity; (5) the time interval during which the target sterilization temperature Ts is maintained; and (6) the value of Ts. It is noted that other factors may affect the values of the time constants.

In embodiments, the time constants $\tau 1$ and $\tau 2$ in Eq. (3) may be determined, considering the factors described above. For instance, test cycles may be repeated to measure temperature while one or more of the factors are varied. Then, using the obtained temperature data, the time constants may be determined/calibrated.

Eq. (3) includes the first and second derivatives of the probe temperature $T_P$ with respect to time. In embodiments, temperature data may be obtained as an array of samples taken at a preset time intervals. Then, the derivatives may be calculated by applying the finite-difference-approximation to the obtained data. In embodiments, a filter, such as low pass filter, may be used to filter the noise in the obtained data before the data is analyzed.

In embodiments, the software application (or algorithm) installed in the mobile device 60 (or, in other suitable external devices) may use Eq. (3) to compensate the lag between the actual ambient gas temperature 84 and measured temperature 82. In FIG. 7, the compensated temperature (or other parameters, such as pressure, humidity, oxygen density, hydrogen peroxide density, etc.) 86 is obtained by compensating the lag in the measured temperature 82, where the compensated temperature 86 indicates that the ambient gas is maintained at Ts during the time interval t3. If t3 is longer than the required time interval for proper sterilization, the compensated temperature 86 correctly indicates that the sterilization cycle passed the test. Thus, the compensation of the lag reduces the rate of false fails.

Figure 10:
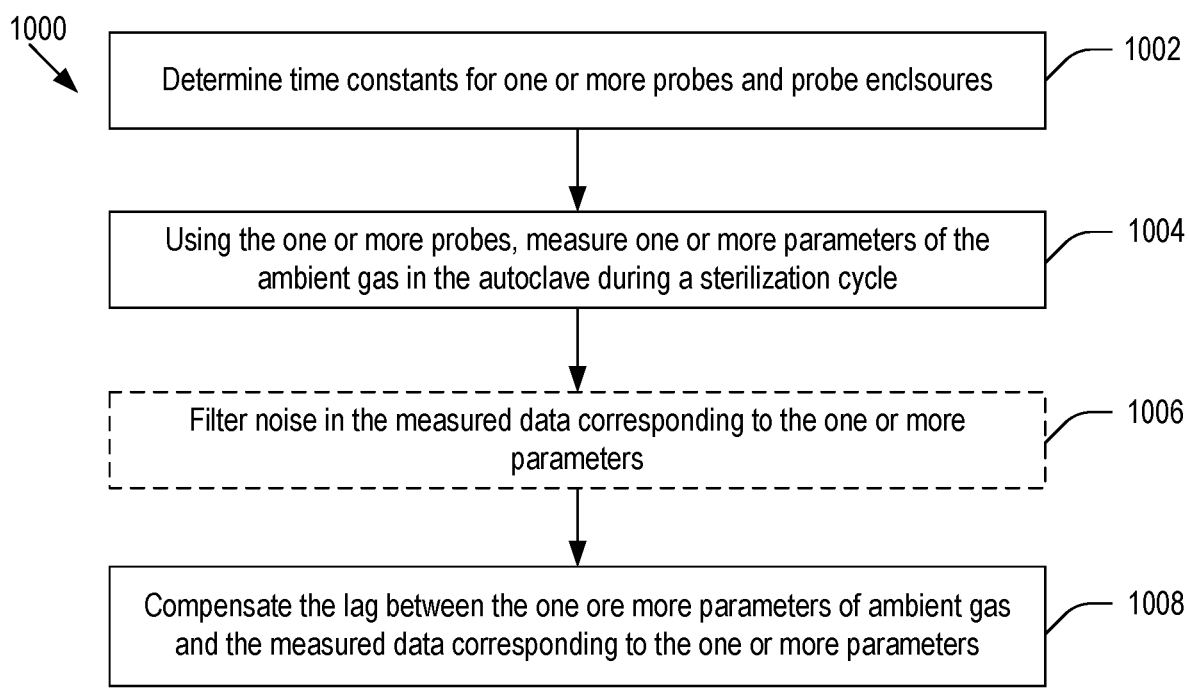
FIG. 10 is a flowchart illustrating exemplary steps that may be carried out to compensate the thermal lag according to embodiments of the present invention.

FIG. 10 is a flowchart 1000 illustrating exemplary steps that may be carried out to compensate the thermal lag (or response lag due to other parameters, such as pressure, humidity, etc.) according to embodiments of the present invention. At step 1002, the time constants, $\tau 1$ and $\tau 2$ in Eq. (3), are determined for each of one or more probes and probe enclosures. In embodiments, the time constants are determined considering various factors that include (1) the location of the package 10 inside the autoclave; (2) whether the package is bagged or unbagged in a pouch during the sterilization cycle; (3) whether the autoclave is unloaded or loaded with other items, such as dental instruments, during the sterilization cycle; (4) whether the autoclave was warm before the cycle; (5) the type of cycles, such as vacuum or gravity; (6) the time interval during which the target sterilization temperature Ts (and/or other ambient gas parameter) is maintained; and (7) the value of Ts (and/or other ambient gas parameter). In embodiments, test cycles may be repeated to measure temperature using the package 10 while one or more of the factors are varied. Then, using obtained data for the measured temperature and/or other parameters, the time constants for the one or more probes may be determined.

Next, at step 1004, using the one or more probe packages, temperature and/or other parameters of the ambient gas in the autoclave is measured at a preset time and/or repeat measurements at a preset time interval. Optionally, the noise in the measured temperature data is filtered out by a filter at step 1006. In embodiments, the filter for each specific probe may or may not be the same, depending on the configuration of the autoclave.

At step 1008, the lag between the actual ambient gas temperature and the measured temperature (and/or between other actual ambient gas parameters and the measured data) is compensated. In embodiments, Eq. (3) may be applied to the measured temperature data in order to generate compensated temperature data, where the compensated temperature data includes reduce thermal lag and thus more accurately shows the actual ambient gas temperature profile.

Figure 11:
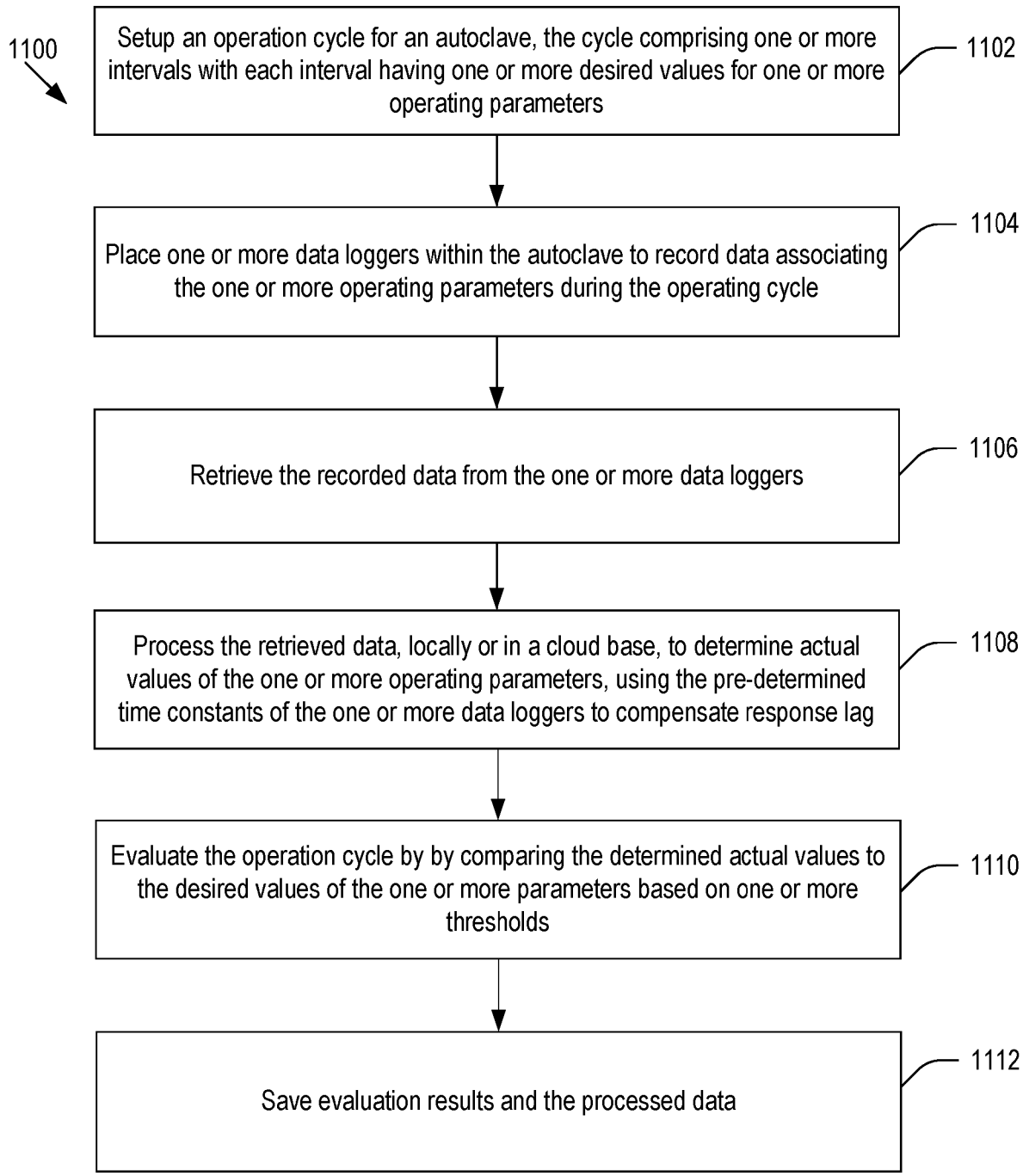
FIG. 11 is a flowchart illustrating exemplary steps to implement autoclave monitoring according to embodiments of the present invention.

FIG. 11 is a flowchart 1100 illustrating exemplary steps to implement autoclave monitoring according to embodiments of the present invention. At step 1102, an operation cycle for the autoclave is setup. The operation cycle may associate with desired values for one or more operating parameters. The operating parameters may be parameters selected from temperature, pressure, humidity, sterilization gas density (such as hydrogen peroxide density), etc. The operating parameters may also comprise time intervals for each of the selected parameters. If a user is running an extended cycle, that may be selected here as well.

At step 1104, one or more data loggers are placed within the autoclave to record data associating with the one or more operating parameters during the operation cycle. In embodiments, the time constants corresponding to response lag of the one or more data loggers are pre-determined using the steps described in FIG. 10.

At step 1106, the measured data for each of the one or more data loggers are retrieved. The data retrieval may be implemented via a wireless link between the probe(s) and a device, as shown in FIG. 5, or via a reader where the probe is docked, as shown in FIG. 6.

At step 1108, the retrieved data are processed, locally or in a cloud base, to determine actual values of the one or more operating parameters, using the pre-determined time constants to compensate response lag of the one or more data loggers. The exemplary method for determining the actual operating parameter value is shown in FIG. 10. In some embodiments, the retrieved data are processed within the logger itself and the results may be indicate by red (fail) and green (pass) LEDs.

At step 1110, the operation cycle is evaluated for operation validity by comparing the determined actual values to the desired values of the one or more parameters based on one or more thresholds. The thresholds may comprises a value threshold for each of the one or more operating parameters and a time interval threshold for which each parameter needs to be maintained. For example, the thresholds for the operation cycle as shown in FIG. 8 may comprises a first temperature threshold, a first interval threshold, a second temperature threshold and a second interval threshold corresponding to the parameters of Ts1, ts1, Ts2 and ts2 respectively. In embodiments, the temperature threshold is configured as a relative threshold. For example, a threshold corresponding to Ts1 is configured such that the measured temperature (preferably after compensation the response lag from the raw measured data using the pre-determined time constants) needs to be within a predetermined percentage (such as ±5%) of Ts1. Similarly, the interval threshold may also be configured such that the compensated measured temperature needs to be maintained at Ts1 with a time period within a predetermined percentage (such as ±5%) of is 1. The percentage for the temperature threshold and the interval threshold may or may not be the same. In embodiments, the operation cycle is determined to be proper (or passed) after all parameter thresholds are met. If any one of the thresholds is not met, the operation cycle is determined to be improper (or failed).

In some embodiments, the one or more thresholds are related to a biological indicator feature. For example, a biological indicator associated with a sterilization cycle may theoretically pass at a $t_B$ interval which is often half the time or less of a time interval setting for an autoclave used to perform the sterilization. At temperature $T_B$, the temperature threshold may then be set as $T_B$ and the interval threshold may be set as $t_B$. When monitoring an autoclave sterilization cycle, the cycle is determined passed as long as the temperature threshold and the interval threshold are met, even though the actual measured time interval is smaller than the time interval setting of the autoclave.

At step 1112, the evaluation result and/or the processed retrieved data are saved, locally or in a cloud storage. The evaluation result may be available to autoclave user, administrator for data achieving, alert, or monitoring. In embodiments, manufacturer may also access the results for quality control.

Figure 12:
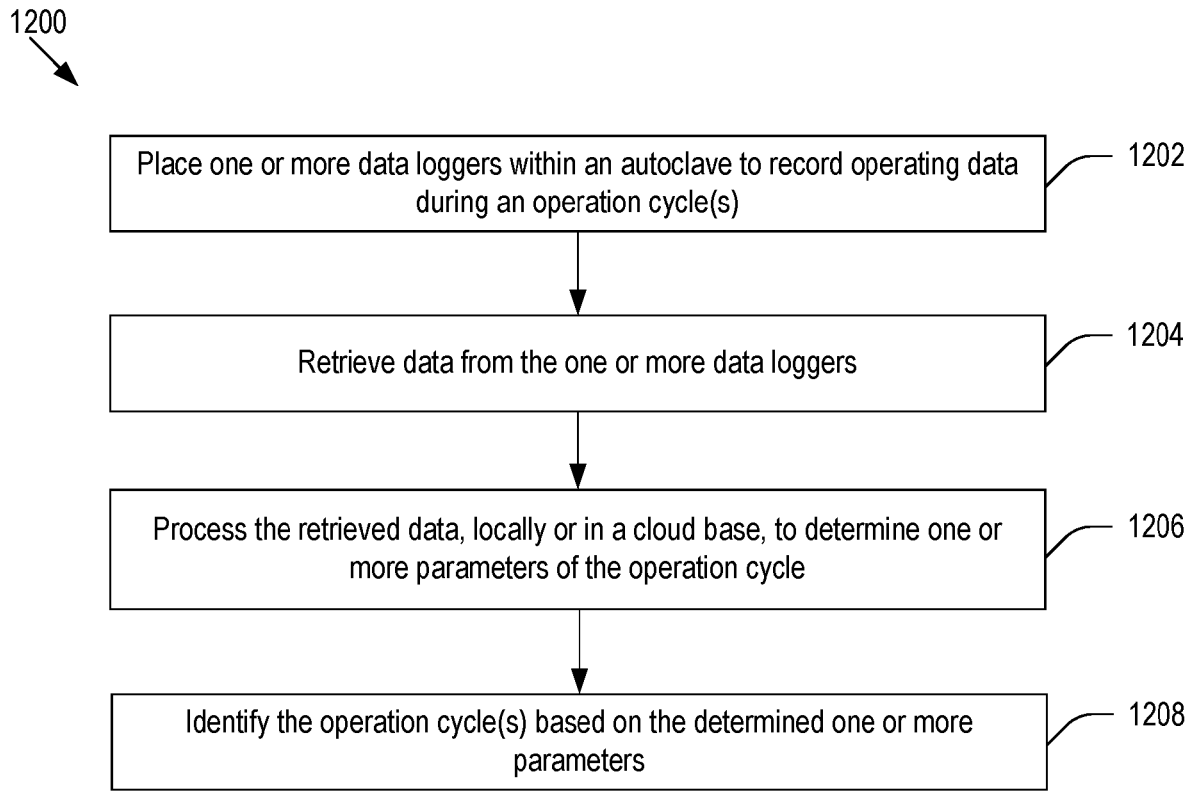
FIG. 12 is a flowchart illustrating exemplary steps for autoclave operation cycle verification according to embodiments of the present invention according to embodiments of the present invention.

In embodiments, some autoclaves do not have programmable capacity for their operation cycles. The user may need to know whether the operation of the autoclave comply with corresponding guidelines, such as the Minimum cycle times for steam sterilization cycles provided by the CDC. Or perhaps some autoclaves do have programmable capacity for their operation cycles, but the user does not wish to pre-select the chosen cycle on data logger software. As a third possibility, a user my not wish to pre-select chosen cycles on data logger software and let the data loggers run for more than one cycle before downloading, processing, and viewing results; an example of this use case is to place one or more data logger(s) in the autoclave in the morning, run cycles throughout the day and download the data logger data only at the end of the day and retrieve the results in bulk. FIG. 12 is a flowchart 1200 illustrating exemplary steps for autoclave operation cycle verification according to embodiments of the present invention according to embodiments of the present invention. At step 1202, one or more probes are placed within an autoclave to log operating data during an operation cycle(s). The details of the operation cycle are to be determined. The operating data may involve one or more parameters, such as ambient gas temperature, pressure, humidity, etc. In embodiments, the time constants corresponding to response lag of the one or more probes may be pre-determined using the steps described in FIG. 10.

At step 1204, the logged operating data for each of the one or more probes are retrieved. The data retrieval may be implemented via a wireless link between the probe and a device or via a reader where the probe is docked.

At step 1206, the retrieved data are processed, locally or in a cloud base, to determine one or more parameters of the operation cycle. The one or more parameters may comprise numbers of distinct intervals, operating parameters and time interval at each interval, etc.

At step 1208, the operation cycle(s) is identified based on the determined one or more parameters. In embodiments, the identification process is implemented by comparing the determined one or more parameters to parameters of reference cycles and selecting the closest match among the reference cycles. In embodiments, the reference cycles are standard guideline cycles, such as the steam sterilization cycles provided by the CDC or those that are FDA approved or approved by some other regulatory body. In embodiments, after the closest match or matches is/are selected, the differences between the determined one or more parameters and the parameters of the selected reference cycle(s) are also evaluated to determine whether the autoclave is running properly. If not, a notice may be sent to the autoclave operator or manufacturer. The user may be queried to verify that the proper cycle(s) has/have been matched, and if not, the matched cycle(s) may be changed according to user intervention. Then the flow chart may transition from step 1208 in FIG. 12 to step 1108 or 1110 in FIG. 11.

Figure 13:
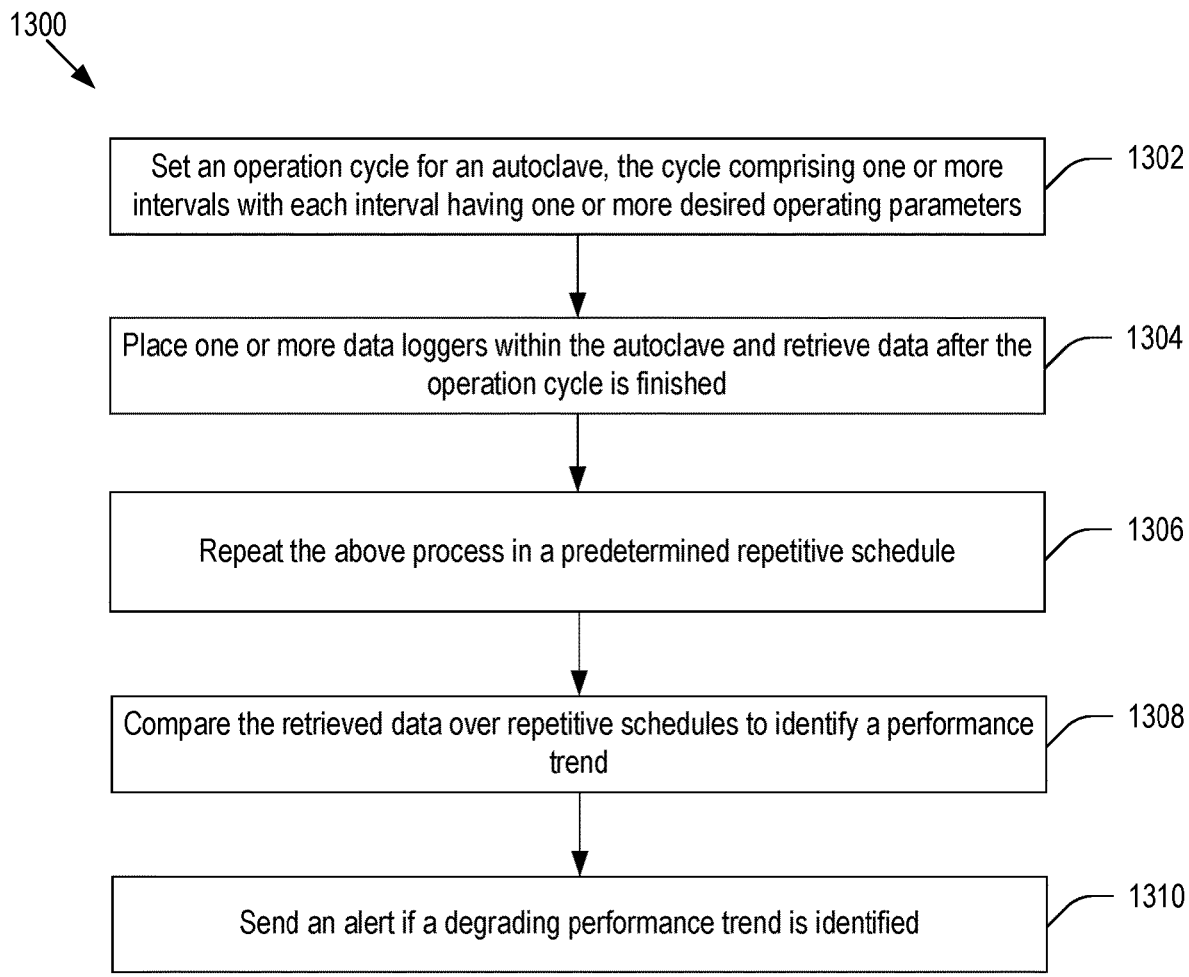
FIG. 13 is a flowchart illustrating exemplary steps for autoclave pre-maintenance according to embodiments of the present invention according to embodiments of the present invention.

FIG. 13 is a flowchart 1300 illustrating exemplary steps for autoclave pre-maintenance according to embodiments of the present invention. At step 1302, an operation cycle for the autoclave is set. The operation cycle may comprise one or more intervals with each interval having one or more desired operating parameters. The operating parameters may be selected from temperature, pressure, humidity, sterilization gas density (such as hydrogen peroxide density), etc.

At step 1304, one or more probes are placed within the autoclave to measure the one or more operating parameters of each interval during the operation cycle and the measured data for each of the one or more probes are retrieved after the operation cycle is finished.

At step 1306, steps 1302 and 1304 are repeated in a predetermined repetitive schedule. The schedule may be based on a daily, weekly, bi-weekly, monthly, or bi-monthly basis. Alternatively, instead of steps 1302, 1304, and 1306, an alternate single step is for a "golden" data logger may be used to record a single cycle as a "golden" benchmark or a trusted initial reference; this would be recorded immediately or very soon after an autoclave is known to be running up to its ideal specifications.

At step 1308, the retrieved data over repetitive schedules are compared to identify a performance trend. The performance trend may reveal information, such as whether the temperature starts to fall below desired temperature setting, whether the autoclave can hold pressure or vacuum during operation, etc.

At step 1310, an alert is generated and sent if a degrading performance trend is identified. In embodiments, the degrading performance trend is identified when logged data over repetitive schedules corresponding to a parameter show a change above a threshold, such as larger than 10%. In embodiments, the degrading performance trend is identified when logged data corresponding to a parameter show an acceleration of change over repetitive schedules. By identifying the performance trend, the autoclave user may detect early signs of fault and may act before any major accident happens.

In embodiments, the data collected during the above autoclave pre-maintenance operations may also be accessible to autoclave manufacturer such that the autoclave manufacturer may know the performance of the autoclaves in real-time and may take early-intervention if necessary.

Figure 14:
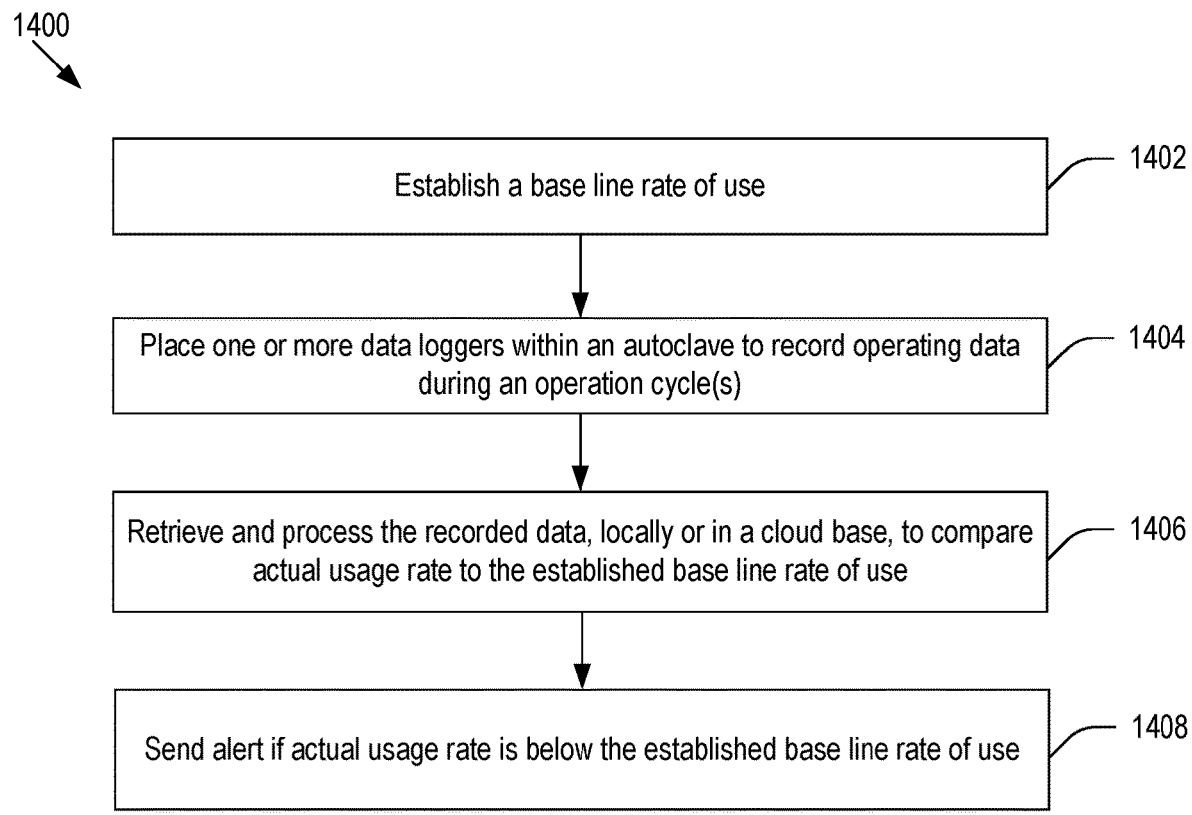
FIG. 14 is a flowchart illustrating exemplary steps for autoclave usage verification according to embodiments of the present invention according to embodiments of the present invention.

FIG. 14 is a flowchart 1400 illustrating exemplary steps for autoclave usage verification according to embodiments of the present invention. In certain usage settings (such as in the medical industry), managers may wonder if every autoclave cycle is being monitored as the subordinates claim to be doing. To electronically make certain of this, in step 1402, a base line rate of use is established as the data logger system is used initially. For example, the typical usage rate may be 5 cycles per day and 25 cycles per week. An algorithm is used to compare the usage rate of the current week versus what is typically run as a norm (this can be a simple arithmetic average). In step 1404, one or more data loggers are placed within an autoclave to record operating data during one or more operation cycles. In step 1406, the recorded data is retrieved and processed, locally or in a cloud base, to compare actual usage rate to the establish base line rate of use. In step 1408, if rate of usage is below the norm or the established base line rate of use, the user may optionally be alerted via text email, or other preferred communication methods. Other time intervals may be selected instead of bi-weekly (e.g., monthly).

In usage settings such as in medical industry, managers may wonder generally if their infection control practices are sufficient. As medical procedures are performed in which utilized instruments become a critical or semi-critical items for risk of infection as defined by the CDC, reprocessing of instruments in autoclave is critical to prevent overall spread of disease. If an autoclave cycle is deemed by the data logger system to have failed (i.e. not have shown the necessary parameters including but not limited to time, temperature and or pressure, humidity, etc.), then the data logger system will first alert the user and manager via a preferred electronic method such as email or text. Then, at the end of an interval as specified by the user (i.e. weekly or monthly), a report is issued either in electronic form or via human communication (i.e. telephone call to the user) that evaluates a number of factors including but not limited to percentage of autoclave cycles that pass or fail over the interval, corresponding percentile versus an de-identified data set, and usage rate; this data is used to provide the user with a recommendation on whether they should take a closer look at their infection control practices, possibly in the form of training by an outside professional.

Additionally, the data collected and analyzed by the data logger system can be provided (either manually or in an automated electronic fashion) to relevant parties such as autoclave manufacturers or regulatory bodies to glean levels of compliance or performance by user or by a more global set of data such as by region or by usage rate. Action can then be taken to improve an issue of poor compliance or poor sterilizer performance. In the case of autoclave manufacturers, they can design future autoclave models to correct for issues gleaned by the data logger system. In the case of a regulator, they can encourage a user to undergo extra training by an infection control professional to improve compliance or instrument reprocessing performance.

In embodiments, the data logger (and/or the whole system) may be used as a process challenge device (PCD). For example, the device may be used in every cycle with a load (i.e. instruments) to ensure their sterility. The device may also be used with or without load whenever a new process, which has not been monitored before, is implemented to ensure the effectiveness of the new process. The device may be also be used to run a cycle without a load to test the process routinely at predetermined schedule, such as at the beginning of the day before any loads are run.

In embodiments, one or more computing system may be configured to perform one or more of the methods, functions, and/or operations presented herein. Systems that implement at least one or more of the methods, functions, and/or operations described herein may comprise an application or applications operating on at least one computing system. The computing system may comprise one or more computers and one or more databases. The computer system may be a single system, a distributed system, a cloud-based computer system, or a combination thereof.

It shall be noted that the present disclosure may be implemented in any instruction-execution/computing device or system capable of processing data, including, without limitation phones, laptop computers, desktop computers, and servers. The present disclosure may also be implemented into other computing devices and systems. Furthermore, aspects of the present disclosure may be implemented in a wide variety of ways including software (including firmware), hardware, or combinations thereof. For example, the functions to practice various aspects of the present disclosure may be performed by components that are implemented in a wide variety of ways including discrete logic components, one or more application specific integrated circuits (ASICs), and/or program-controlled processors. It shall be noted that the manner in which these items are implemented is not critical to the present disclosure.

Figure 15:
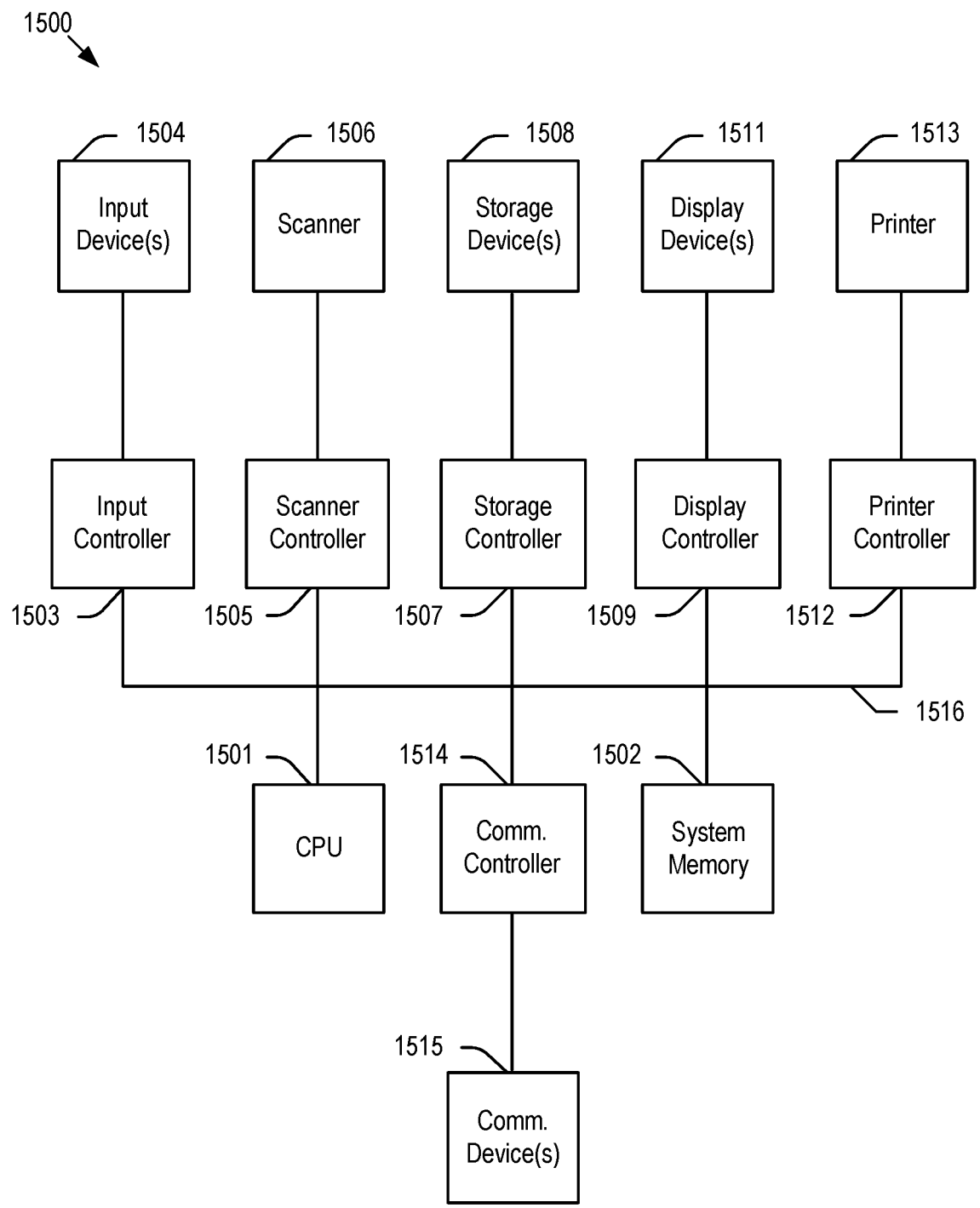
FIG. 15 shows a computer system according to embodiments of the present invention.

Having described the details of the disclosure, an exemplary system 1500, which may be used to implement one or more aspects of the present disclosure, will now be described with reference to FIG. 15. Each client/server in FIG. 15 includes one or more components in the system 1500. As illustrated in FIG. 15, system 1500 includes a central processing unit (CPU) 1501 that provides computing resources and controls the computer. CPU 1501 may be implemented with a microprocessor or the like, and may also include a graphics processor and/or a floating point coprocessor for mathematical computations. System 1500 may also include a system memory 1502, which may be in the form of random-access memory (RAM) and read-only memory (ROM).

A number of controllers and peripheral devices may also be provided, as shown in FIG. 15. An input controller 1503 represents an interface to various input device(s) 1504, such as a keyboard, mouse, or stylus. There may also be a scanner controller 1505, which communicates with a scanner 1506. System 1500 may also include a storage controller 1507 for interfacing with one or more storage devices 1508 each of which includes a storage medium such as magnetic tape or disk, or an optical medium that might be used to record programs of instructions for operating systems, utilities and applications which may include embodiments of programs that implement various aspects of the present disclosure. Storage device(s) 1508 may also be used to store processed data or data to be processed in accordance with the disclosure. System 1500 may also include a display controller 1509 for providing an interface to a display device 1511, which may be a cathode ray tube (CRT), a thin film transistor (TFT) display, or other type of display. System 1500 may also include a printer controller 1512 for communicating with a printer 1513. A communications controller 1514 may interface with one or more communication devices 1515, which enables system 1500 to connect to remote devices through any of a variety of networks including the Internet, an Ethernet cloud, an FCoE/DCB cloud, a local area network (LAN), a wide area network (WAN), a storage area network (SAN) or through any suitable electromagnetic carrier signals including infrared signals.

In the illustrated system, all major system components may connect to a bus 1516, which may represent more than one physical bus. However, various system components may or may not be in physical proximity to one another. For example, input data and/or output data may be remotely transmitted from one physical location to another. In addition, programs that implement various aspects of this disclosure may be accessed from a remote location (e.g., a server) over a network. Such data and/or programs may be conveyed through any of a variety of machine-readable medium including, but are not limited to: magnetic media such as hard disks, floppy disks, and magnetic tape; optical media such as CD-ROMs and holographic devices; magneto-optical media; and hardware devices that are specially configured to store or to store and execute program code, such as application specific integrated circuits (ASICs), programmable logic devices (PLDs), flash memory devices, and ROM and RAM devices.

Embodiments of the present disclosure may be encoded upon one or more non-transitory computer-readable media with instructions for one or more processors or processing units to cause steps to be performed. It shall be noted that the one or more non-transitory computer-readable media shall include volatile and non-volatile memory. It shall be noted that alternative implementations are possible, including a hardware implementation or a software/hardware implementation. Hardware-implemented functions may be realized using ASIC(s), programmable arrays, digital signal processing circuitry, or the like. Accordingly, the "means" terms in any claims are intended to cover both software and hardware implementations. Similarly, the term "computer-readable medium or media" as used herein includes software and/or hardware having a program of instructions embodied thereon, or a combination thereof. With these implementation alternatives in mind, it is to be understood that the figures and accompanying description provide the functional information one skilled in the art would require to write program code (i.e., software) and/or to fabricate circuits (i.e., hardware) to perform the processing required.

It shall be noted that embodiments of the present disclosure may further relate to computer products with a non-transitory, tangible computer-readable medium that have computer code thereon for performing various computer-implemented operations. The media and computer code may be those specially designed and constructed for the purposes of the present disclosure, or they may be of the kind known or available to those having skill in the relevant arts. Examples of tangible computer-readable media include, but are not limited to: magnetic media such as hard disks, floppy disks, and magnetic tape; optical media such as CD-ROMs and holographic devices; magneto-optical media; and hardware devices that are specially configured to store or to store and execute program code, such as application specific integrated circuits (ASICs), programmable logic devices (PLDs), flash memory devices, and ROM and RAM devices. Examples of computer code include machine code, such as produced by a compiler, and files containing higher level code that are executed by a computer using an interpreter. Embodiments of the present disclosure may be implemented in whole or in part as machine-executable instructions that may be in program modules that are executed by a processing device. Examples of program modules include libraries, programs, routines, objects, components, and data structures. In distributed computing environments, program modules may be physically located in settings that are local, remote, or both.

One skilled in the art will recognize no computing system or programming language is critical to the practice of the present disclosure. One skilled in the art will also recognize that a number of the elements described above may be physically and/or functionally separated into sub-modules or combined together.

It will be appreciated to those skilled in the art that the preceding examples and embodiment are exemplary and not limiting to the scope of the present disclosure. It is intended that all permutations, enhancements, equivalents, combinations, and improvements thereto that are apparent to those skilled in the art upon a reading of the specification and a study of the drawings are included within the true spirit and scope of the present disclosure.

What is claimed is:

1. A method for evaluating an operating cycle of an autoclave, the method comprising:
    in a first operating cycle of an autoclave, using a plurality of sensors to measure a set of operating parameters that indicate a condition associated with the autoclave;
    applying to at least some of the set of operating parameters compensation parameters associated with at least one of the plurality of sensors and the autoclave to compensate one or more of the set of operating parameters; and
    based on target data having one or more threshold values and being associated with the condition, evaluating the condition by comparing the compensated parameters to the target data to obtain a first evaluation result.

2. The method according to claim 1, wherein the set of operating parameters comprises at least one of a temperature, a pressure, a humidity, and a sterilization gas density.

3. The method according to claim 1, further comprising, based on the first evaluation result, generating an alert signal that indicates a difference between the compensated parameters and the target data.

4. The method according to claim 1, further comprising, based on the first evaluation result, selecting a second operating cycle to obtain a second evaluation result.

5. The method according to claim 1, wherein the compensation parameters comprise a time constant associated with a thermal lag between at least one of a sensor temperature and an actual temperature.

6. The method according to claim 1, wherein the set of operating parameters comprises a time interval corresponding to at least one operating parameter.

7. The method according to claim 1, wherein the target data comprises target time interval that defines at least a part of the operating cycle.

8. The method according to claim 1, wherein evaluating the condition is performed by a device that is external to the autoclave.

9. The method according to claim 8, wherein the device receives at least some of the set of operating parameters via wireless communication.

10. The method according to claim 1, wherein the compensation parameters are determined prior to the first operating cycle.

11. A system for evaluating an operating cycle of an autoclave, the system comprising:
    an autoclave comprising a chamber;
    one or more sensors located within the chamber, the one or more sensors measure within a first operating cycle a set of operating parameters that indicate a condition associated with the autoclave; and one or more data loggers coupled to the plurality of sensors, the one or more data loggers performing the steps of:

recording the set of operating parameters;

applying to at least some of the set of operating parameters compensation parameters associated with at least one of the autoclave and the one or more sensors to compensate one or more of the set of operating parameters;

obtaining target data associated with the condition; and evaluating the condition by comparing, based on one or more threshold values, the compensated parameters to the target data to obtain a first evaluation result.

12. The system according to claim 11, wherein the one or more data loggers, based on the first evaluation result, generate an alert that indicates a difference between the compensated parameters and the target data.

13. The system according to claim 12, wherein at least some of the compensation parameters are pre-determined.

14. The system according to claim 11, wherein the one or more data loggers are configured to operate two or more operating cycles.

15. The system according to claim 11, wherein the set of operating parameters comprises at least one of a temperature, a pressure, a humidity, and a sterilization gas density.

16. The system according to claim 11, wherein the at least one of the one or more data loggers is a process challenge device.

17. The system according to claim 11, wherein the one or more threshold values define at least one of a temperature range and a time range.

18. The system according to claim 11, wherein the target data comprises target time interval that defines at least some of the operating cycle.

19. The system according to claim 11, further comprising an external device that evaluates the condition, the external device being external to the autoclave.

20. The system according to claim 19, wherein the one or more data loggers are coupled to the external device to communicate at least some of the set of operating parameters via a wireless communication interface.

* * * * *